US005854255A

United States Patent [19]
Cincotta et al.

[11] Patent Number: 5,854,255
[45] Date of Patent: *Dec. 29, 1998

[54] THERAPEUTIC PACKAGE FOR THE LONG TERM REDUCTION OF BODY FAT STORES INSULIN RESISTANCE HYPERINSULINEMIA AND HYPERGLYCEMIA IN VERTEBRATES

[75] Inventors: Anthony H. Cincotta, Andover, Mass.; Albert H. Meier, Baton Rouge, La.

[73] Assignees: Ergo Research Corporation, Wakefield, R.I.; The Board of Supervisors of Louisiana State University and Agricultural and Mechanical College, Baton Rouge, La.

[ * ] Notice: The term of this patent shall not extend beyond the expiration date of Pat. No. 5,731,312.

[21] Appl. No.: 843,760

[22] Filed: Apr. 21, 1997

Related U.S. Application Data

[63] Continuation of Ser. No. 468,528, Jun. 6, 1995, Pat. No. 5,731,312, which is a continuation of Ser. No. 249,808, May 26, 1994, Pat. No. 5,554,623, which is a continuation of Ser. No. 719,745, Jun. 24, 1991, Pat. No. 5,344,832, which is a continuation-in-part of Ser. No. 463,327, Jan. 10, 1990, abandoned, which is a continuation-in-part of Ser. No. 192,332, May 10, 1988, abandoned.

[51] Int. Cl.$^6$ .......................... A61K 31/44; A61K 31/495
[52] U.S. Cl. .......................... 514/280; 514/250; 514/288; 514/866; 514/909
[58] Field of Search ................................... 514/280, 250, 514/288, 866, 909

[56] References Cited

U.S. PATENT DOCUMENTS

| | | | |
|---|---|---|---|
| 3,074,847 | 1/1963 | Bigsby et al. | 514/271 |
| 3,722,383 | 3/1973 | German Larsent et al. | 31/495 |
| 3,752,814 | 8/1973 | Fluckiger et al. | 514/346 |
| 3,752,888 | 8/1973 | Fluckiger et al. | 514/250 |
| 3,922,347 | 11/1975 | Bach et al. | 514/288 |
| 4,054,660 | 10/1977 | Clemens et al. | 514/288 |
| 4,239,763 | 12/1980 | Milavec et al. | 514/250 |
| 4,659,715 | 4/1987 | Meier et al. | 514/288 |
| 4,749,709 | 6/1988 | Meier et al. | 514/288 |
| 4,783,469 | 11/1988 | Meier et al. | 514/288 |
| 5,006,526 | 4/1991 | Meier et al. | . |
| 5,344,832 | 9/1994 | Cincotta et al. | 514/288 |
| 5,498,803 | 3/1996 | Meier et al. | . |
| 5,554,623 | 9/1996 | Cincotta et al. | 514/288 |

FOREIGN PATENT DOCUMENTS

| | | |
|---|---|---|
| 890369 | 3/1982 | Belgium . |
| 57-82317 | 9/1980 | Japan . |
| 2192541 | 1/1988 | United Kingdom . |

OTHER PUBLICATIONS

Cassar, J. et al. "Bromocriptine Treatment of Acromegaly," *Metabolism* 26:539–546 (1977).
Dolocek, R. et al. "Bromocriptine and glucose tolerance in acromegalics," *Pharmatherapeutica* 3: 100–106 (1982).
Eskildsen, P.C. et al. "Long–Term Treatment of Acromegaly with Bromocriptine," *Acta Endocr.* 87:687–700 (1978).
Steinbeck, K. and J.R. Turtle, "Treatment of Acromegaly-with Bromocryptine," *Aust. N.Z. J. Med.* 9: 217–224 (1979).
Wass, J.A.H. et al. "An Assessment of Glucose Intolerance In Acromegaly and Its Response to Medical Treatment," *Clin. Endocr.* 12: 53–59 (1980).
Harel et al., *Proc. La. Acad. of Sci.*, 38:125, 1975.
Joseph et al., *Proc. Soc. Exp. Biol. Med.*, 146:1150–1155, 1974.
Komorowski et al., *Aliment. Nutr. Metab.*, 1(4):293, 1980.
Larsson et al., *Lakartidningen (Sweden)*, 82(50):4425, 1985.
Martin et al., *The Condor*, 75:369–374, 1973.
Martin et al., "Hormonal Control of Orientation in the White–Throated Sparrow, *Zonatrichia Albicollis.*" *Chronobiology*, pp. 641–646, 1974.
Martin et al., *Proc. La Acad. of Sci.*, 38:127, 1975.
Martin et al., *Am. Zoologist*, 18(3):572, 1978.
Martin, D., "Hormonal Regulation of Migratory Orientation in the White–Throated Sparrow, *Zonatrichia Albicollis.*" Diss. LSU, 1974.
Martin, D., "Factors Influencing the Circadian Rhythm of Locomotor Activity in the Anabatoid Fish, *Trichogaster Trichopterus Sumatranus.*" Thesis. Sam Houston State College, 1969.
Meier et al., *Experientia*, 48:248–253, 1992.
Meier et al., *Physiol. Zool.*, 41(1):95–103, 1968.
Southern et al., *J. Anim. Sci.*, 68:931–936, 1990.
*Acta. Diabetol. Lat.*, vol. No. 26(2), pp. 133–145, 1989.
Bansal et al., *Chem. Abstracts* 96(11) Abstract No. 80405f.
Barnett, *Post Graduate Medical J.* 56:11–14, 1980.
Bartness et al., *J. Exp. Zoology* 244:437–454, 1987.
Berle, *Acta Endocr. Suppl.* 173, Abstract No. 104, 1973.

(List continued on next page.)

*Primary Examiner*—Kevin E. Weddington
*Attorney, Agent, or Firm*—Darby & Darby

[57] ABSTRACT

A therapeutic package for dispensing to, or for use in dispensing to, a vertebrate being treated for a metabolic condition selected from the group consisting of obesity, insulin resistance, hyperinsulinemia, and hyperglycemia comprising one or more unit doses of bromocriptine and labeling directing the use of the package in the treatment of the metabolic condition in a dosage regimen under which the delivery of the bromocriptine is confined to the period during the day near the time of day at which the serum prolactin concentration of a lean, insulin sensitive vertebrate of the same sex is low, and further directing the use of said package in conjunction with the concomitant administration to the vertebrate of one or more unit doses providing a therapeutically effective amount of a prolactin stimulator in a dosage regimen under which the delivery of the prolactin stimulator is confined to the period during the day after the time at which the serum prolactin concentration of a lean, insulin-sensitive vertebrate of the same sex reaches its lowest point and prior to the time of day when the prolactin concentration rises to a peak in lean, insulin-sensitive vertebrates of the same sex.

22 Claims, No Drawings

OTHER PUBLICATIONS

Burns et al., *Gen. Pharmac.* 10;173–176, 1979.
Carey et al., *Chem. Abstracts* 91(5) Abstract No. 36590k.
Carey et al., *Chem. Abstracts.* 93(13) Abstract No. 125921c.
Caveizel et al., *Abstract & Acta Diabetol. Lat.* 26(2):133–145, 1989 (abstract only translation).
(1979) *Chemical Abstracts*, vol. No. 91, No. 5, Abstract No. 36590k.
(1980) *Chemical Abstracts*, vol. No. 93, No. 13, Abstract No. 125921c.
(1981) *Chemical Abstracts*, vol. No. 95, No. 1, Abstract No. 530j.
(1982) *Chemical Abstracts*, vol. No. 97, No. 19, Abstract No. 156398a.
(1982) *Chemical Abstracts*, vol. No. 96, No. 11, Abstract No. 80405f.
(1982) *Chemical Abstracts*, vol. No. 97, No. 3, Abstract No. 17600w.
(1984) *Chemical Abstracts*, vol. No. 101, No. 7, Abstract No. 49205p.
(1988) *Chemical Abstracts*, vol. No. 109, Abstract No. 66888w.
(1990) *Chemical Abstracts,* vol. No. 112, No. 21, Abstract No. 191532p.
(1990) *Chemical Abstracts*, vol. No. 112, Abstract No. 75773u.
Cincotta et al. *Life Sciences* 45:2247–2254, 1989.
Cincotta et al. *Ann Nutr Metab* 33:305–314, 1989.
Cincotta et al. *Horm Metabol Res* 21;64–68, 1989.
Cincotta et al., *Chem. Abstracts* 112(2) Abstract No. 75773u.
Cincotta et al., *J. Endocrinol.* 120:385–391, 1989.
Cincotta et al., *Experientia* 43:416–417, 1987.
Cincotta, *J. Endocrinol.* 103:141–146, 1984.
Cincotta et al. *J. Endocrinol.* 106:177–181, 1985.
Cincotta et al. *J. Endocrinol.* 106:173–176, 1985.
Eisemann et al., *J. of Animal Sci.* 59(1)86–94, 1984.
Eisemann et al., *J. of Animal Sci.* 59(1)95–104, 1984.
Emata et al., *J. Exp. Zoology* 233:29–34, 1985.
Fang, V.S., *Chem. Abstracts.* 95(1), Abstract No. 530j.
Fitzgerald et al., *Chem. Abstracts* 97(3) Abstract No. 17600w.
Grigoriev et al.,*Aviat. Space Envir. Med.* pp. 302–305, 1988.
Haisenleder et al., *Proc. Soc. Exp. Biol. & Med.* 4:1818–1819, 1988.
Harter et al., *Chem. Abstracts* 89(14), Abstract No. 213108r.
Horseman et al., *General and Comparative Endocrinology* 38:269–274, 1979.
Horseman et al., *J. Endocr.* 82:367–372, 1979.
John et al., *Phy. Zool.* 45(1):34–42, 1972.
Joseph et al., *J. Exp. Zool.* 178(1):59–62, 1971.
Jungmann et al., *Chem. Abstracts* 97(19) Abstract No. 156398a.
Lawson et al., *Endocrin.* 96:313–318, 1975.
Lee et al., *J. of Exp. Zool.* 166(3):307–317, 1967.
Lobato et al. *Mol. and Cell. Biochem.* 67:19–23, 1985.
Mannelli, M., *Chem. Abstracts* 101(7) Abstract No. 49205p.
Meier, *Gen. & Comp. Endocrin. Suppl.* 2:55–62, 1969.
Meier et al., *Amer. Zool.* 16:649–659, 1976.
Meier et al., *General and Comparative Endocrinology* Suppl. 3:499–508, 1972.
Meier, *Proc. Symp.*, pp. 647–651, Nov. 8–10, 1971.
Meier et al., *Current Ornithology* 2:303–343, 1984.
Meier et al., *Science* 173:1240–42, 1971.
Meier et al., *Proc. Soc. Exp. Biol. and Med.* 133(4):1113–16, 1970.
Meier et al., *Gen. & Comp. Endocrin.* 17:311–318, 1971.
Meier et al., *Gen. & Comp. Endocrin.* 8(1):110–114, 1967.
Meier et al., *Proc. Soc. for Exp. Biol. & Med.* 137:408–415, 1971.
Meier et al., *Amer. J. of Physiology* 232(2):E193–E196, 1977.
Meier et al., *Biology of Reproduction* 8:400–410, 1973.
Meier et al., *Transactions of the American Fisheries Society* 113:422–431, 1984.
Meier et al., *General and Comparative Endocrinology* 26:253–258, 1975.
Meier et al., Circadian hormone basis for seasonal conditions in the gulf killifish *Fundulus grandis*. In *Comparative Endocrinology*, pp. 141–144. Galliard et al. (eds), Elsevier/North Holland Biomedical Press, Amsterdam (1978).
Meier, *Amer. Scientist* 61 (2)184–187, 1973.
Miller et al., *J. Interdiscipl. Cycle Res.* 14(1):75–84, 1983.
Miller et al., *J. Interdiscipl. Cycle Res.* 14(2):85–94, 1982.
Moore et al., *Biology of Reproduction* 36:47–58, 1987.
Ottenweller et al., *Life Sciences* 28:1033–1040, 1981.
Spieler et al. *Life Sciences* 22:255–258, 1977.
Steinbeck, K. and J.R. Turtle, "Treatment of Acromegaly-with Bromocryptine," *Aust. N.Z. J. Med.*9: 217–224 (1979).
Thomas et al., *Sem. des Hosp. de Paris.* 53(34–35):1857–1862, 1977 (abstract only translation).
Wass, J.A.H. et al. "An Assessment of Glucose Intolerance In Acromegaly and Its Response to Medical Treatment," *Clin. Endocr.* 12:53–59 (1980).
Wilson, *Chrono. Bio. Int.* 6:113–121, 1989.
El–Densharg et al., Chemical Abstracts, 106:188934, 1987.

THERAPEUTIC PACKAGE FOR THE LONG TERM REDUCTION OF BODY FAT STORES INSULIN RESISTANCE HYPERINSULINEMIA AND HYPERGLYCEMIA IN VERTEBRATES

This is a continuation of application Ser. No. 08/468,528, filed Jun. 6, 1995, U.S. Pat. No. 5,731,312 which is a continuation of application Ser. No. 08/249,808, filed May 26, 1994, now U.S. Pat. No. 5,554,623 which is a continuation of application Ser. No. 07/719,745, filed Jun. 24, 1991, now U.S. Pat. No. 5,344,832, which is a continuation-in-part of application Ser. No. 07/463,327 filed Jan. 10, 1990, now abandoned, in turn a continuation-in-part of application Ser. No. 07/192,332 filed May 10, 1988, now abandoned.

1. Field of the Invention

This invention relates to an improved process for the reduction in vertebrates, animals or humans, of body fat stores, and reduction of insulin resistance, hyperinsulinemia, which is often associated with insulin resistance, and hyperglycemia, or reduction of plasma glucose. In particular, it relates a process requiring the timed daily administrations of a dopamine agonist and a prolactin stimulator at appropriate preselected times of day, and preferably also a thyroid hormone, to reduce and control over an extended period the stated pathologies which, with obesity, are pathologies characteristic of the onset of noninsulin dependent, or Type II diabetes.

2. Background

In U.S. Pat. No. 4,659,715, which issued Apr. 21, 1987 to Albert H. Meier and Anthony H. Cincotta, there is disclosed a method for the reduction in vertebrate animals of body fat stores, without concomitant decrease in muscle mass, via the administration of multiple daily doses over prescribed periods of a prolactin-inhibiting, or dopamine compound. This method, which is associated with an altered lipid metabolism, offers hope to those suffering with obesity; a serious worldwide health problem.

In pending U.S. application Ser. No. 463,327, supra, there is disclosed a method, or process, for the long term modification and regulation of lipid metabolism in a vertebrate, animal or human, not only to reduce obesity, but also to reduce insulin resistance, and hyperinsulinemia or hyperglycemia, or both, by administration to a subject of a prolactin-inhibiting compound, or dopamine agonist. The role of prolactin in a vertebrate species to control these pathologies (the hallmarks of noninsulin dependent, or type II diabetes), it was found, was crucial! The level of prolactin in the blood of a species is time-of-day, dependent, and cyclic, its level in the blood rising and falling at different times of day dependent on the amount of fat deposited in the body of the subject. The phrase relationships between the rise and fall of prolactin which appears in the blood streams of obese and lean subjects, respectively, are different. Administration of the dopamine agonist, it is disclosed, is made over a limited period at a time of day dependent on the normal circadian rhythm of fat and lean members, respectively, of a similar species based on the result to be achieved. Where, e.g., it is desired to reduce the body fat of a subject, decreases in body fat deposits are produced by treatment of the obese species on a timed daily sequence based on circadian rhythms of the peak prolactin, or peak prolactin and peak glucocorticosteroid, blood level established for lean members of a similar species. A person, whether lean or obese, showing the effects of insulin resistance, or hyperinsulinemia and/or hyperglycemia, or both insulin resistance and hyperinsulinemia and/or hyperglycemia, treated with the dopamine agonist or prolactin-inhibiting compound, in the same manner as a person suffering with obesity, it was found would become more sensitive to insulin, and the effects of hyperinsulinemia and/or hyperglycemia would be reduced on a long term basis. Thus, insulin resistance, and hyperinsulinemia or hyperglycemia, or both, like obesity, can be controlled in humans on a long term basis by treatments corresponding to that for the treatment of obesity to lower fat deposits in the body of the subject.

Albeit the administration to obese subjects of a prolactin-inhibiting compound on a time-of-day schedule related to a daily prolactin secretion cycle mimicking that of a lean subject to cause the obese subject to lose body fat, the results have proven less than 100 percent effective. For example, in treating a large population of obese subjects to reduce body fat during the winter months, a significant reduction in body fat occurred in the majority of the treated patients. On the other hand, it was observed that a lower percentage of a population of obese patients similarly treated during the summer months showed a significant reduction in body fat. This suggests that prolactin secretions in a subject are to some extent seasonal, but equally if not more important it suggests that better timing and control of prolactin secretions in a subject, particularly during the summer months, can improve and render more effective the liboregulatory nature of the treatments to reduce obesity, reduce insulin resistance, and hyperinsulinemia or hyperglycemia, or both.

3. Objects.

It is, accordingly, a primary objective of this invention to provide further improvements in a method for the long term modification and regulation of lipid, metabolism to alter, phase shift and reset on a long term, or permanent basis, circadian hormonal timing mechanisms in the neural centers of the brain.

In particular, it is an object to provide a process for resetting the circadian neural center of vertebrate animals, including humans, to alter neural centers which stimulate and control prolactin secretion to produce long lasting changes in the amount of body fat stores, the sensitivity of the cellular response of a species to insulin, and overcome hyperinsulinemia and/or hyperglycemia, which generally accompanies insulin resistance.

A more specific object is to provide a process for resetting the circadian neural centers of animals, including humans, which regulate and control lipogenesis to decrease obesity and maintain the more normal body fat stores of a lean animal, or lean human, on a long term basis.

A further, and equally specific object is to provide a process for resetting on a long term basis the circadian neural centers, particularly in humans, which regulate and control the sensitivity and responsiveness of the cells to insulin, and suppress hyperinsulinemia or hyperglycemia, or both.

4. The Invention

These objects and others are achieved in accordance with this invention, a process which embodies in addition to the administration of a dopamine agonist, e.g. L-DOPA or bromocriptine, on a timed daily basis to modify and reset the neural circadian oscillation expressed by the prolactin rhythm (prolactin oscillation) of a vertebrate animal, or human subject, or both the prolactin and glucocorticosteroid (glucocorticosteroid oscillation) rhythms of said subject, administering on a timed daily basis at a different predetermined time of day a prolactin stimulator, e.g. metoclopramide (Reglan), in dosage amount sufficient to increase hormonal prolactin secretion in the blood of the subject to better control and regulate the prolactin rhythm, or both the prolactin and glucocorticosteroid rhythms, of the subject. Administration of the dopamine agonist, continued on a daily basis over a sufficient period of time, as disclosed in application Ser. No. 463,327, supra, can be employed to increase the hyperglycemia sensitivity to insulin, reduce body fat stores, suppress hyperinsulinemia and reduce hyperglycemia in a subject, to reset long term on cessation of the daily dosages of the dopamine agonist the neural phase oscillation of the prolactin rhythm, or both the prolactin and glucocorticosteroid rhythms, in a subject; and the administration of the dopamine agonist and additionally the prolactin stimulator at a different predetermined time of day can be employed to control, regulate and reset on a long term basis these circadian neural hormonal expression, and correct these pathologies, with higher consistency and greater effectiveness than by administration of the dopamine agonist alone. In treating a large subject population of obese person, during the summer months when the success rate is lower than the winter months, with a dopamine agonist alone to regulate lipid metabolism and reduce fat deposits in the bodies of these subjects, success was achieved in about 60 percent of the patients treated. In contrast, in treating a second large subject population of obese persons over a similar period of time during the summer months with a similar dopamine agonist and additionally, a prolactin stimulator, success was achieved in about 85 percent of the population, an improvement of about 25 percent. The weight loss of body fat in a group treated with both the dopamine agonist and the prolactin stimulator, measured on a weekly basis during the period of treatment, is almost double that of the group treated with the dopamine agonist alone.

The efficacy of treatment with the dopamine agonist and prolactin stimulator can also be improved by daily thyroid hormone administration to a subject; particularly hypothyroid subjects. Exemplary thyroid hormones are, e.g., thyroxine, triiodothyronine, synthroid and other thryoxine analogs. The thyroid hormones are given daily, once a day, suitably in the morning after waking. Suitably, the thyroid hormone is given at dosage levels ranging from about 0.1 to about 0.4 milligrams per day, preferably from about 0.2 to about 0.35 milligrams per day.

In the practice of this invention, the dopamine agonist, or prolactin-inhibiting compound, and prolactin stimulator are administered daily to a subject orally or by subcutaneous, intravenous or intramuscular injections, at different times of day, to alter the prolactin rhythm from that of a lean subject to that of an obese subject of the same species, or as is most often the objective to alter the prolactin rhythm from that of an obese subject to that of a lean subject of the same species. In treating a subject to alter, reset, and phase shift the prolactin rhythm from that of an obese subject to that of a lean subject, administration of the dopamine agonist and prolactin stimulator can not only be employed to reduce body fat stores or obesity, in an obese subject, but also to reduce insulin resistance, hyperinsulinemia or hyperglycemia, or both hyperinsulinemia and hyperglycemia, in a subject, obese or lean, exhibiting any one, or all of these symptoms desirable of change. In carrying out this process, where it is desired to modify, phase shift, and reset the prolactin rhythm of a subject to that of a lean animal, to reduce body fat stores if the subject is obese, increase sensitivity response to insulin whether the subject is lean or obese, and suppress hyperinsulinemia or hyperglycemia, or both, whether the subject is lean or obese, the dopamine agonist is administered in daily dosage amount sufficient to decrease, or reduce hormonal prolactin secretion in the blood of the subject at a time or just after the time of day corresponding to that when the prolactin level in the blood of a lean insulin sensitive subject is at a pea, and the prolactin stimulator is administered in dosage amount sufficient to increase hormonal prolactin secretion in the blood of the subject at a time or near the time of day when the prolactin level in the blood of a lean insulin sensitive subject is at its lowest point, or point of maximum depression; this occurring just before the prolactin level rises to a peak in a lean insulin sensitive subject. Thus, a prolactin-inhibiting compound, preferably an ergot-related prolactin-inhibiting compound, is administered to a subject exhibiting any one or more of the symptoms desirable of change, e.g., obesity, insulin resistance, hyperinsulinemia or hyperglycemia at a time of day when plasma prolactin levels are low in lean insulin sensitive subjects of the same species. Exemplary of prolactin-inhibiting, ergot-related compounds are: 2-bromo-alpha-ergocryptine; 6-methyl-8 beta-carbobenzyloxy-aminoethyl-10 alpha-ergoline; 8-acylaminoergolenes, such as 6-methyl-8 alpha-(N-acyl) amino-9-ergoline and 6-methyl-8 alph-(N-phenylacetyl) amino-9-ergoline; ergocornine; 9,10-dihydroergocornine; and D-2-halo-6-alkyl-8-substituted ergolines. e.g., D-2-bromo-6-methyl-8-cyanomethylergoline. Moreover, the non-toxic salts of the prolactin-inhibiting ergot-related compounds formed from pharmaceutically acceptable acids are also useful in the practice of this invention. Bromocriptine, or 2-bromo-alpha-ergocryptine, has been found particularly useful in the practice of this invention. A prolactin stimulator is administered to the same subject just before that time of day when daily plasma prolactin levels are highest in lean insulin sensitive subjects of the same species (i.e., before the onset of sleep. Exemplary of prolactin stimulators are dopamine antagonists, i.e. metoclopramide, haloperidol, pimozide, phenothiazine, sulpiride, chlorpromazine and serotonin agonists, i.e. MAO inhibitors, e.g. pargyline, synthetic morphine analogs, e.g. methadone, antiemetics, e.g. metoclopramide, antipsychotics, e.g. sulpiride, estrogens and others, e.g. tryptophan and 5-hydroxy-tryptophan.

In the treatment of an animal, or human subject, the stores of body fat can be depleted or increased, the treatments continued until the stores of body fat are stabilized at an optimum or near optimum level dependent on the level of body fat stores desired in the subject, for time sufficient that on termination of the treatment the prolactin rhythm, and preferably both the prolactin and glucocorticosteroid rhythms, are reset to maintain on a long term basis the reduced, or increased, body weight stores. In humans, the objective is almost invariably to reduce body fat stores, and obesity. It has been established that a relationship exists between obesity and insulin resistance, and that obesity can lead to increased insulin resistance. Likewise, it has been established that the circadian rhythms of plasma prolactin and glucocorticosteroid concentrations, respectively, differ in lean and fat animals as well as in insulin sensitive animals and animals that are insulin resistant (decreased insulin stimulated glucose disposal). In a fat animal, prolactin will reach a peak level at a give hour of a 24 hour period (in a human, usually near midday), and the prolactin level of a lean animal at another time of day (in a human usually during sleep). In a lean animal the glucocorticosteroid, e.g., cortisol, will peak during a 24 hour period at a given hour (generally at a time different from that of prolactin); in a human generally several hours after waking. Thus, the phase relations of the cortisol and prolactin rhythms differ in lean and fat animals. The peak periods of prolactin and glucocorticosteroid production, respectively, may differ to some extent between males and females of any given species. In carrying out the invention process, a daily dosage of a dopamine agonist, or prolactin inhibitor, is given to an obese subject shortly after the normal time of day that the prolactin is at its peak in a lean insulin sensitive subject of the same species and sex, and daily dosages of a prolactin stimulator are given to the same obese subject (in conjunction with the prolactin inhibitor) shortly before the normal time of day that the prolactin is at its peak in a lean insulin sensitive subject of the same species and sex, to produce a body fat weight reduction in the obese subject. Such treatments will, if continued over a sufficient period, reset on a long term or permanent basis the phase of the neural oscillation for the prolactin rhythm, or the phases of the neural oscillations for both the prolactin and glucocorticosteroid rhythms in the obese insulin resistant subject to that present in a lean insulin sensitive subject. The obese subject, on initiation of the treatment with the dopamine agonist, or prolactin inhibitor in conjunction with the prolactin stimulator, will lose body fat stores, and the body fat deposits of the obese subject on continuation of the treatments on a daily basis will drop to and stabilize at that of a lean subject of the same species. On discontinuing the daily treatments, the rise and fall of the prolactin, or prolactin and glucocorticosteroid levels in the blood of the treated patient on a daily basis will correspond to that of a lean insulin sensitive subject of the same species, and for a period of long duration. The effect of resetting the prolactin, or prolactin and glucocorticosteroid rhythms, in this manner in a subject exhibiting any one or more of the symptoms desirable of change, i.e., insulin resistance, hyperinsulinemia or hyperglycemia, whether the subject is lean or obese (and loses body fat stores) also increases the sensitivity of the cells of the subject to insulin, reduces hyperinsulinemia or hyperglycemia, or both, and thus alters long term pathologies which are characteristics of the onset of Type II diabetes.

In treating vertebrates, generally, dosages of the dopamine agonist, and prolactin stimulator, respectively, are each given, generally once a day, on a daily basis, generally over a period ranging from about 10 days to about 150 days. The dopamine agonist is given daily at dosage levels ranging from about 3 micrograms to about 100 micrograms, preferably from about 8 micrograms to about 20 micrograms, per pound of body weight, and the prolactin stimulator is given daily at dosage levels ranging from about 10 micrograms to about 100 micrograms, preferably from about 20 micrograms to about 50 micrograms, per pound of body weight to modify, or alter, and continued for a time sufficient to reset the circadian plasma prolactin rhythm.

In treating humans, the dopamine agonist, or prolactin inhibitor, is generally given at daily dosage levels ranging from about 3 micrograms to about 20 micrograms, preferably from about 4 micrograms to about 12 micrograms, per pound of body weight, and the prolactin stimulator is generally given at daily dosage levels ranging from about 10 micrograms to about 100 micrograms, preferably from about 20 micrograms to about 50 micrograms, per pound of body weight. Such treatments continued over a period of time ranging from about 30 days to about 60 days will modify and reset the lipid and glucose metabolism of the obese person to that of a lean person, if given to an obese person daily so that the prolactin inhibitor is given just a short period after the typically daily peak of plasma prolactin concentration in a lean person and the prolactin stimulator is given a short period before plasma prolactin peaks in a lean person. Body fat deposits, inclusive of adipose, arterial wall and plasma fat, within the obese person will be reduced, leveled out and maintained after the treatments are discontinued at that of a lean person, over an extended period of time. A person showing the effects of insulin resistance, or hyperinsulinemia and/or hyperglycemia, or both insulin resistance and hyperinsulinemia and/or hyperglycemia, treated with the dopamine agonist, or prolactin inhibitor, and a prolactin stimulator at similarly appropriate times of day, will become more sensitive to insulin (i.e., will have a lower insulin resistance), and the effects of hyperinsulinemia and/or hyperglycemia will be reduced on a long term basis. The injections of the dopamine agonist, or prolactin inhibitor, and prolactin stimulator, in this manner will thus reset the phase relations of the two neural oscillations and their multiple circadian expressions to alter metabolism on a long term basis, if not permanently. In other words, there will be as a result of the timed daily dosages of the dopamine agonist, or prolactin inhibitor, and prolactin stimulator, a long term reversal of the major pathologies generally associated with the development of Type II diabetes. The levels of body fat stores, plasma insulin concentrations, insulin resistance, and hyperglycemia, or all of these pathologies can be reduced on a long term basis by such treatment, or treatments, from the high levels often found in obese, hyperinsulinemia persons to that of the much lower and much more desirable levels found in lean euinsulinemic persons.

The dopamine agonist is administered to a subject, particularly a human, exhibiting symptoms to be controlled at a time, or just after the time the prolactin concentration reaches its peak in the plasma of a lean subject, particularly a lean insulin sensitive subject, generally within about 2 hours to about 8 hours, preferably within about 4 hours to about 6 hours after the peak would occur in a lean subject, particularly a lean insulin sensitive subject. The prolactin stimulator is administered at a time just before the plasma prolactin rhythm found in a lean subject reaches its pea, generally from about 2 hours to about 4 hours, preferably from about 2 hours to about 3 hours, before the plasma protein has reached it peak in a lean person. Administration of the prolactin stimulator just before sleep has been found highly satisfactory.

The responsiveness of the timed daily treatments with the dopamine agonist and prolactin stimulator can be further improved by the administration of daily dosages of thyroid hormones, particularly in the treatment of hypothyroid subjects or subjects whose blood during certain times of the year appear deficient in thyroid hormones. It is known, e.g., that the circadian rhythm of response to prolactin depends on adequate thyroid hormone (John, Meier and Bryant, *Physiological Zoology* 45, pp. 34–42, 1972); and that the circadian rhythms of cortisol and prolactin responses are also dependent on thyroid hormone (Meier, *Endocrinology* 98, pp. 1474–1479, 1976; Ottenweller and Hedge, *Life Sciences* 28, pp. 1023–1040, 1981). Studies have shown that the further administration of thyroid hormones on a daily basis with the dopamine agonist and prolactin stimulator increase the responsiveness of many hypothyroid, near hypothyroid, and seasonally hypothyroid subject types of such treatments. It is accordingly a further preferred feature of this invention to administer once a day on a daily basis, besides the dopamine agonist and prolactin stimulator, thyroid hormone at dosage levels ranging from about 0.1 milligrams to about 0.4 milligrams, preferably from about 0.2 milligrams to about 0.35 milligrams, the levels of body fat, plasma triglyceride plasma cholesterol and the symptoms, or pathologies associated with Type II diabetes can be lowered on a long term basis by such treatment; and the treatment rendered more effective in hypothyroid individuals.

In terms of the human subject, "obesity can be defined as that body weight over twenty percent above the ideal body weight for a given population" (R. H. Williams, *Textbook of Endocrinology*, 1974, pp. 904–916). The time of day when the prolactin and glucocorticosteroid levels, respectively, will peak in the blood of humans during the day differs between obese subjects and lean subjects, and the peak in each type of subject can be readily determined by measurement of the fat and lean specimens, as defined. In other animal species what constitutes obese and lean members, respectively, of a species can be readily determined by body weight patterns correlated with the prolactin and glucocorticosteroid levels, respectively, in the plasma of lean and obese members, respectively. The levels differ between members of the different species, but among members of the same species there is close correlation between prolactin and glucocorticosterone levels, respectively, at certain times of the day dependent on the obesity or leanness of a given specimen.

These and other features of the invention will be better understood by reference to the following information and data of experimental work with animals and humans. In the examples the terminology "LD" refers to the light/dark cycle, the first number following the expression LD refers to the hours of light, and the second to the hours of darkness in the cycle. Thus LD 14:10 refers to a cycle having 14 hours of light and 10 hours of darkness, and this period of the day is expressed in terms of 2400 hours. The letter n refers to the number of animals in a group, "BW" designates body weight, g represents grams, mg represents milligrams, and "ub" is an expression of micrograms.

In the following examples, data are given which show the altered phase relationships of the circadian rhythms of plasma corticosteroid and prolactin concentrations; changes beneficial in the treatment of diabetics.

EXAMPLE 1

A 44 year old obese woman weighting 198 pounds was given bromocriptine tablets (2.5 mg/day), taken orally, shortly after waking in the morning, and metoclopramide tablets (10 mg/day), taken orally, just before sleep late at night. After 6 weeks of treatment, body weight was reduced by 5 pounds without dieting or increased exercise. The percentage body far determined by skinfold measurements was reduced from 35.4 to 32.3. This reduction is equivalent to a loss of 7.7 pounds of body fat, from 70.0 pounds to 62.3 pounds. Loss of fat exceeding loss of body weight is a general characteristic of this treatment that sharply differentiates it from diet programs in which considerably protein, carbohydrate and water is lost in addition to fat.

EXAMPLE 2

A hypothyroid 58 year old woman who was mildly obese responded poorly to bromocriptine (1.25 mg) taken orally daily 2 hours after waking for 3 months. A change in treatment to a combination of bromocriptine and metoclopramide (Reglan), a prolactin stimulator, in conjunction with an increase of thyroid hormone (Synthroid from 0.2 to 0.35 mg daily, produced dramatic losses in both body fat stores and body weight. Oral dosages of bromocriptine (1.25 mg) were taken daily 2 hours after waking and metoclopramide (5 mg) was taken orally immediately before sleep. Synthroid was taken orally (0.35 mg/day) within 2 hours after waking. After 6 weeks, body weight was reduced from 161 to 145 pounds without a restriction on food consumption or increased exercise regimen. Body fat stores determined by skinfold measurements was reduced by 8.5 pounds, from a total fat content of 53.8 pounds to 45.3 pounds. The subject claimed she had not been so lean or weighed so little in 22 years. Further decreases in body fat and body weight were evident after 20 weeks of treatment. Weight was reduced from 161 lbs (initial to 125 lbs and fat was reduced by a total of 20.6 lbs. In addition, plasma concentrations of total cholesterol and triglyceride were reduced by such treatment after 20 weeks, the initial and final cholesterol levels were 237 and 152 mg/dl, respectively. The initial and final triglyceride levels were 1191 and 161 mg./dl, respectively. This combination of prolactin inhibitor (bromocriptine), prolactin stimulator (metoclopramide) and thyroid hormone has been found especially useful for resetting circadian rhythms in hypothyroid individuals who have rhythms of low amplitude that are resistant to resetting by bromocriptine alone.

EXAMPLE 3

A 57 year old obese woman was given orally 1.25 mg bromocriptine daily one hour after waking and 10 mg metoclopramide shortly before sleep. After 2 weeks, body weight was reduced from 194 to 189 and percentage body fat, determined from skinfold measurements, was reduced from 39.5 and 38.1. The fat loss, then, in 2 weeks was 4.6 pounds, accounting for almost all of the body weight loss.

EXAMPLE 4

A 63 years old obese woman was given orally 1.24 mg bromocriptine daily at one hour after waking and 2.5 mg bromocriptine 6 hours after waking. Metoclopramide (10 mg) was given orally immediately before sleep. After 19 days, percentage body fat, determined by skinfold measurements, was reduced from 37.1 to 35.5. This is a loss of 2.1 pounds of fat without food restriction, increased exercise or loss of body weight.

EXAMPLE 5

A 60 year old obese woman with Type II diabetes was given orally 1.25 mg bromocriptine daily at one hour after waking and 10 mg metoclopramide immediately before sleep. After 6 weeks, body fat was reduced from 108.3 lbs (initial) to 97.9 lbs. Fasting blood glucose levels were reduced from 126 mg/dl (initial) to normal levels (near 100 mg/dl). Furthermore, the daily dose of the hypoglycemic drug she took for treatment of diabetes (micronase) was reduced from 5.0 to 2.5 mg midway during the bromocriptine/metoclopramide treatment.

EXAMPLE 6

An obese 55 year old man weighing 285 pounds with Type II diabetes was given orally 2.5 mg bromocriptine daily one hour after waking and 10 mg metoclopramide immediately before sleep. He lost 11 pounds of fat during 8 weeks of treatment. Fasting blood glucose levels were 180 mg/dl prior to treatment. After 4 weeks of treatment, blood glucose levels were near normal (100 mg/dl) and diabetic treatment with a hypoglycemic drug (miconase) was discontinued. After 8 weeks of bromocriptine and metoclopramide treatment, the fasting glucose was 104 mg/dl.

EXAMPLE 7

Three post menopausal women (Subjects A, B and C) with high initial levels of body fat (40.6, A; 37.1, B; and 39.5, C, % body weight), as indicated by skinfold measurements, were treated orally with 1.25 mg bromocriptine taken within one hour of waking and 5 mg metoclopramide taken immediately before sleep. Body fat was reduced by 5.8 lbs after 7 weeks (Subject A), 5.1 lbs after 5 weeks (Subject B) and 6.5 lbs after 4 weeks (Subject C).

EXAMPLE 8

Two control groups of adult human subjects, a first control group of seven patients was treated daily through the warm months with bromocriptine alone, and a second control group of ten patients was treated during the same period daily with both bromocriptine and metoclopramide. In the first control group the bromocriptine was administered once a day orally in dosage levels of 1.25 mg and 2.5 mg, respectively, in the morning just after waking. The second group was similarly treated, except that each person in this group was additionally given daily by mouth at bedtime 10 mg of the metoclopramide. The treatments were continued daily over periods ranging up to 16 weeks. During the period of treatment the body fat content of each patient was determined from skinfold measurements (supralliac, subscapular, triceps and biceps). The number of weeks of treatment, the total decrease in body fat (lbs.) during the period, and the average body fat loss (lbs.) per week for each individual of the two groups are given in the Table.

TABLE

Reductions of Body Fat in Adult Human Subjects[1] Treated with Bromocriptine Alone, and Both Bromocriptine and Metoclopramide, Respectively

| Treatment | Initials of Subjects | Weeks of Treatment | Decrease in Body Fat (lbs) | Fat Loss Per Week (lbs) |
|---|---|---|---|---|
| Bromo- | PC | 9 | 3.5 | 0.39 |
| criptine | JL | 12 | 5.3 | 0.44 |
| | FB | 6 | 8.8 | 1.47 |
| | JA | 6 | 1.7 | 0.28 |
| | JW-1 | 8 | 5.1 | 0.64 |
| | JW-2 | 8 | 1.9 | 0.24 |
| | BH | 6 | 2.0 | 0.33 |
| | Mean ± SEM | 7.8 ± 2.2 | 4.0 ± 2.6 | 0.54 ± 0.17 |
| Bromo- | MM | 6 | 4.6 | 0.77 |
| criptine + | AM-1 | 16 | 16.5 | 1.03 |
| Meto- | TC | 3 | 6.4 | 2.13 |
| clopramide | MH | 6 | 3.1 | 0.52 |
| | BR | 3 | 3.7 | 1.23 |
| | WH | 6 | 3.1 | 0.52 |
| | AM-2 | 5 | 5.1 | 1.02 |
| | LG | 4 | 6.5 | 1.62 |
| | HG | 5 | 3.7 | 0.74 |
| | JW | 8 | 5.8 | 0.72 |
| | Mean ± SEM | 6.2 ± 3.1 | 5.9 ± 3.3 | 0.95 ± 0.16[2] |

[1]Mean body weight was 175 lbs and mean % body fat, initially, was 33.5 (58.6 lbs fat).
[2]This value differs ($p < 0.05$; Student's t) from that of subjects treated with bromocriptine, alone.

These data show that the average body fat loss per week for the group treated with both bromocriptine and metoclopramide was essentially double that of the group treated with bromocriptine alone. Moreover, the total decrease in body fat over the period was higher for the group treated with both bromocriptine and metoclopramide. It was found that the treatment of a subject with both bromocriptine and metoclopramide vis-a-vis treatment of a subject with bromocriptine alone is more effective during the summer months than during the winter months.

The dates show that metabolic states are regulated at least in part by an interaction of circadian neuroendocrine rhythms. It is believed that the daily rhythms of cortisol and prolactin are individual expression of two separate circadian systems and that the daily injections of these hormones can reset the phase relations of these two systems. Thus, in a hamster model it has been found that the 0-hour relation resets the circadian oscillations into a pattern that maintains the lean, insulin sensitive state and the 12-hour relation permits retention of a pattern that maintains the obese, insulin resistant state. The effects of timed injections of a dopamine agonist, or prolactin-inhibiting compound, it has been found are long lasting. Apparently once reset, the phase relation of the two circadian oscillations tends to maintain its altered pattern.

Changes in the phase relations of two circadian neuroendocrine oscillations are evidenced by changes in the phase relations of their circadian expression. This expression is fulfilled respecting plasma glucocorticosteroid and prolactin rhythms. In several species examined, the phase relations of the two hormone rhythms differ in lean and fat animals.

The phase relation between the circadian rhythm of plasma insulin concentration and the rhythm of lipogenic responsiveness to insulin is shown to differ in lean and fat animals. Whereas the daily interval of lipogenic responsiveness remains near light onset, the phase of the insulin rhythm varies markedly. The peak concentration of insulin, e.g. occurs near light onset in obese female hamsters held on short day lengths. That is, the daily peas of the lipogenic stimulus (i.e., insulin) and the lipogenic response to insulin coincide in fat animals and not in lean animals.

The phase relations of both prolactin and insulin rhythms as well as the rhythms of tissue responses to the hormones are important elements in the regulation of lipogenesis. Phase malfunctions in these and perhaps other rhythms may also account for insulin resistance.

It is apparent that various modification and changes can be made without departing the spirit and scope of this invention.

Having described the invention, what is claimed is:

1. A therapeutic package for dispensing to, or for use in dispensing to, a patient being treated for a metabolic condition selected from the group consisting of obesity, insulin resistance, hyperinsulinemia, and hyperglycemia comprising:

one or more unit doses, each such unit dose comprising an amount of bromocriptine therein such that periodic administration of one or more of said unit doses is effective to treat said metabolic condition, and a finished pharmaceutical container therefor,
said container containing said unit dose or doses,
said container further containing or comprising labeling,
said labeling directing the use of said package in the treatment of said metabolic condition in a dosage regimen under which the delivery of said bromocriptine is confined to the period during the day proximate to the time of day at which the serum prolactin concentration of a lean, insulin sensitive patient of the same sex is low, and further directing the use of said package in conjunction with the concomitant administration to said patient of one or more unit doses providing a therapeutically effective amount of a prolactin stimulator in a dosage regimen under which the delivery of said prolactin stimulator is confined to the period during the day after the time at which the serum prolactin concentration of a lean, insulin-sensitive patient of the same sex reaches its point of maximum depression and prior to the time of day when said prolactin concentration rises to a peak in lean, insulin-sensitive patients of the same sex.

2. A package according to claim 1 in which the delivery of said bromocriptine is directed to be confined proximate to the time of waking and the delivery of said prolactin stimulator is confined proximate to the time of onset of sleeping.

3. A package according to claim 1 in which one or more unit doses of said prolactin stimulator is contained in said pharmaceutical container.

4. A therapeutic package for dispensing to, or for use in dispensing to, a patient being treated for a metabolic condition selected from the group consisting of obesity, insulin resistance, hyperinsulinemia, and hyperglycemia comprising:

one or more unit doses, each such unit dose comprising an amount of bromocriptine therein such that periodic administration of one or more of said unit doses is effective to treat said metabolic condition, and a finished pharmaceutical container therefor, said container containing said unit dose or doses, said container further containing or comprising labeling, said labeling directing the use of said package in the treatment of said metabolic condition in a dosage regimen under which the delivery of said bromocriptine is confined to the period during the day proximate to the time of day at which the serum prolactin concentration of a lean, insulin sensitive patient of the same sex is low.

5. A package according to claim 4 in which the delivery of said bromocriptine is directed to be confined proximated to the time of waking.

6. A package according to claim 4 wherein said labeling directs the use of said package in the treatment of obesity.

7. A package according to claim 4 wherein said labeling directs the use of said package in the treatment of insulin resistance.

8. A package according to claim 5 wherein said labeling directs the use of said package in the treatment of obesity.

9. A package according to claim 5 wherein said labeling directs the use of said package in the treatment of insulin resistance.

10. In a therapeutic package providing (a) one or more unit doses of bromocriptine as an active ingredient thereof, and (b) a finished pharmaceutical container that contains said unit dose or unit doses, said container further containing or comprising labeling directing the use of said package in the treatment of a human disease or condition, the improvement which comprises:

labeling directing the use of said package by a patient exhibiting a metabolic condition selected from the group consisting of obesity, insulin resistance, hyperinsulinemia, glucose intolerance, and hyperglycemia by periodic administration of one or more of said unit doses using a dosage regimen under which the delivery of bromocriptine is confined to the period during the day proximate to the time day at which the serum prolactin concentration of a lean, insulin-sensitive individual of the same sex is low.

11. A package according to claim 10 wherein said labeling further directs the use of said package in conjunction with the concomitant administration to said patient of one or more unit doses providing a therapeutically effective amount of a prolactin stimulator in a dosage regimen under which the delivery of said prolactin stimulator is confined to the period during the day at which the serum prolactin concentration of a lean, insulin-sensitive patient of the same sex reaches its point of maximum depression and prior to the time of day when said prolactin concentration rises to a peak lean, insulin sensitive patients of the same sex.

12. A package according to claim 10 in which the delivery of said bromocriptine is directed to be confined proximate to the time of waking.

13. A package according to claim 10 wherein said labeling directs the use of said package in the treatment of obesity.

14. A package according to claim 10 wherein said labeling directs the use of said package in the treatment of insulin resistance.

15. A package according to claim 12 wherein said labeling directs the use of said package in the treatment of obesity.

16. A package according to claim 12 wherein said labeling directs the use of said package in the treatment of insulin resistance.

17. A package according to claim 6 in which said dosage regimen consists essentially of one timed daily dose.

18. A package according to claim 17 in which said dosage regimen comprises administration on a substantially uninterrupted basis for at least several months.

19. A package according to claim 4 in which said dosage regimen consists essentially of a single timed daily dose administered from about 4 hours to about 8 hours after the time at which serum prolactin concentrations would typically peak in a lean, insulin-sensitive individual of the same sex as said patient.

20. An improvement or package according to claim 7 in which said dosage regimen consists essentially of one timed daily dose.

21. An improvement or package according to claim 20 in which said dosage regimen comprises administration on a substantially uninterrupted basis for at least several months.

22. An improvement or package according to claim 10 in which said dosage regimen consists essentially of a single timed daily dose administered from about 4 hours to about 8 hours after the time at which serum prolactin concentrations would typically peak in a lean, insulin-sensitive individual of the same sex as said patient.

* * * * *